(12) United States Patent
Iino et al.

(10) Patent No.: US 8,628,783 B2
(45) Date of Patent: Jan. 14, 2014

(54) METHOD FOR GROWING FIBROBLASTS

(75) Inventors: Masato Iino, Yokohama (JP); Satoshi Amano, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 13/593,683

(22) Filed: Aug. 24, 2012

(65) Prior Publication Data

US 2012/0328648 A1 Dec. 27, 2012

Related U.S. Application Data

(62) Division of application No. 12/867,771, filed as application No. PCT/JP2009/001447 on Mar. 30, 2009, now abandoned.

(51) Int. Cl.
*A61K 36/064* (2006.01)

(52) U.S. Cl.
USPC .................. 424/195.16; 424/401; 424/778

(58) Field of Classification Search
None
See application file for complete search history.

(56) References Cited

U.S. PATENT DOCUMENTS

| | | | |
|---|---|---|---|
| 4,803,800 | A | 2/1989 | Romaine et al. |
| 6,207,694 | B1 | 3/2001 | Murad |
| 6,461,857 | B1 | 10/2002 | Scholz et al. |
| 6,858,212 | B2 | 2/2005 | Scholz et al. |
| 2004/0109880 | A1 | 6/2004 | Pauly et al. |
| 2007/0134265 | A1 | 6/2007 | Takada et al. |
| 2008/0300529 | A1* | 12/2008 | Reinstein ................ 604/20 |
| 2009/0136540 | A1 | 5/2009 | Takada et al. |

FOREIGN PATENT DOCUMENTS

| | | |
|---|---|---|
| CN | 1921823 | 2/2007 |
| JP | 6-23088 | 3/1994 |
| JP | 8-163983 | 6/1996 |
| JP | 2000-319122 | 11/2000 |
| JP | 2000-319189 | 11/2000 |
| JP | 2002-356435 | 12/2002 |
| JP | 2003137763 A * | 5/2003 |
| JP | 2003-342124 | 12/2003 |
| JP | 2004-519208 | 7/2004 |
| JP | 3641699 | 4/2005 |
| JP | 3748941 | 12/2005 |
| JP | 3839438 | 8/2006 |
| JP | 2007-210915 | 8/2007 |
| JP | 2008-184441 | 8/2008 |
| KR | 10-2007-0066452 | 6/2007 |
| KR | 10-0803924 | 2/2008 |
| WO | 2004/075621 | 9/2004 |

OTHER PUBLICATIONS http://www.lonza.com/products-services/personal-care/biotechnological-actives/biodynes-empp.aspx—accessed May 30, 2013.*

Espace Patent Abstract for JP Publication No. 2008184441 published Aug. 14, 2008, one page.
Espace Patent Abstract for JP Publication No. 9295928 published Nov. 18, 1997, one page.
Espace Patent Abstract for WO Publication No. 2004075621 published Sep. 10, 2004, one page.
Espace Patent Abstract for JP Publication No. 61171405 published Aug. 2, 1986, one page.
Espace Patent Abstract for JP Publication No. 8163983 published Jun. 25, 1996, one page.
Espace Patent Abstract for JP Publication No. 2005232022 published Sep. 2, 2005, one page.
Espace Patent Abstract for JP Publication No. 200319189 published Nov. 21, 2000, one page.
Espace Patent Abstract for JP Publication No. 2002356435 published Dec. 13, 2002, one page.
Espace Patent Abstract for JP Publication No. 2003342124 published Dec. 3, 2003, one page.
Espace Patent Abstract for JP Publication No. 2004519208 published Jul. 2, 2004, one page.
Espace Patent Abstract for JP Publication No. 200319122 published Nov. 21, 2000, one page.
International Search Report for corresponding PCT/JP2009/001447 mailed Jun. 16, 2009, four pages.
European Communication dated May 30, 2012, Application No. 09700092, Applicant—Shiseido Company, Ltd., one page.
Third Party Observation under Article 115 EPC of the Council of Scientific & Industrial Research from India, signed by V.K. Gupta, thirty-six pages, 2012.
Extended European Search Report, Application No. 09700092, Dated Jul. 4, 2012, 7 pages.
Database WPI, Week 200648, Thomson Scientific, London, GB; AN 2006-468859, XP002678688, 1 page, 2006.
Database WPI, Week 200929, Thomson Scientific, London, GB; AN 2009-H36958, XP002678689, 2 pages, 2009.
Database WPI, Week 199635, Thomson Scientific, London, GB; AN 1996-348971, XP002678690, 2 pages, 1996.
Database WPI, Week 200851, Thomson Scientific, London, GB; AN 2008-J01686, XP002678691, 1 page, 2008.
D.A. Muravyeva, "Variability of the Chemical Composition of Medicinal Plants", Pharmacognosy, Moscow Medicine, p. 23, 1978, 8 pages.
Russian Office Action and English Translation dated Nov. 29, 2012, 11 pages.
Chinese Office Action and Partial English Translation dated Nov. 28, 2012, 14 pages.
English Abstract of KR 10-0803924, published Feb. 15, 2008, 1 page.
European Office Action, Application No. 09700092.1, dated Jun. 13, 2013, 4 pages.
Japanese Office Action, Application No. 2009-548134, dated Jun. 25, 2013, with partial English translation, 4 pages.
English Abstract of JP 2002-356435, 1 page, 2002.
English Abstract of JP 2007-210915, 1 page, 2007.
Chinese Office Action and partial English translation dated Aug. 26, 2013, 5 pages.

* cited by examiner

*Primary Examiner* — Susan Hoffman
(74) *Attorney, Agent, or Firm* — Rankin, Hill & Clark LLP

(57) ABSTRACT

A method for reducing the occurrence of wrinkles in skin caused by aging by promoting the growth of fibroblasts, which have a declined cellular proliferative potential due to aging or adverse affects from ultraviolet light or active oxygen. The method includes the steps of providing an agent that contains a yeast extract and a safflower extract as effective constituents, and applying the agent to skin to promote the growth of fibroblasts.

4 Claims, 1 Drawing Sheet

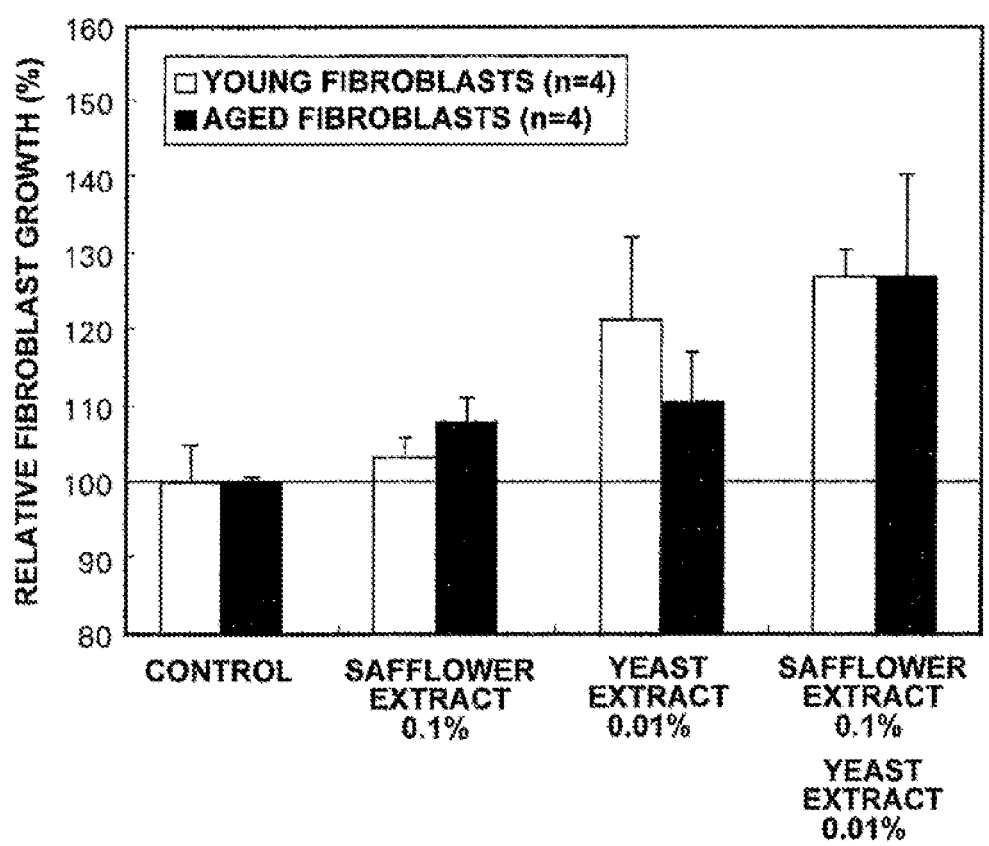

METHOD FOR GROWING FIBROBLASTS

CROSS-REFERENCE TO RELATED APPLICATIONS

This application is a division of U.S. application Ser. No. 12/867,771, Aug. 18, 2010, now abandoned, which is a 371 of PCT/JP2009/001447, filed Mar. 30, 2009.

TECHNICAL FIELD

This invention relates to an agent for growing fibroblasts. This invention particularly relates to an agent for growing fibroblasts capable of promoting the growth of aged fibroblasts. This invention also relates to an external preparation for skin, which preparation contains the agent for growing fibroblasts.

BACKGROUND ART

Recently, keeping the healthy and beautiful skins has become a matter of great concern without distinction of age or sex. The skin is principally classified into three layers, i.e., the epidermis, the derma, and the hypodermic tissue. Of the three layers, the derma is markedly important for keeping the skin structure. The derma is a binding tissue having a structure in which, principally, fibroblasts, collagen fibers, elastic fibers (elastin), and the like, spread in a composite, three-dimensional pattern. The proteins, such as collagen, which constitute the fibers, are produced by the fibroblasts. The fibroblasts keep the balance of synthesis and decomposition of the proteins and keep the condition of the binding tissue. The strength, the stretchability, and the elasticity of the skin are thereby maintained.

Due to internal factors, such as aging, and external factors, such as ultraviolet light and active oxygen, the binding tissue of the derma decreases, and the functions which the skin keeps originally, such as contractibility, flexibility, and moisturizing character, become weak. As a result, various troubles of the skin, such as the occurrence of wrinkles and sagging, and the lowering of suppleness and elasticity, occur. It is considered that the important factors for the skin aging symptoms as described above are the decrease of the number of the fibroblasts of the derma of the skin, the lowering of the functions of the fibroblasts of the derma of the skin, and the decrease of matrix fibers which are produced by the fibroblasts. Therefore, in order for an anti-aging external preparation for skin having an action of preventing and improving skin aging to be obtained, attempts have heretofore been made to search and blend a constituent having a function of promoting the growth of fibroblasts.

For example, in cited literatures 1 and 2, it is reported that extracts of plants, such as *Lens esculenta, Piper longum, Centella asiatica, Ocimum sanctum, Ocimum tenuiflorum,* and *Ocimurn album,* and a hibiscus extract have the fibroblast growth activity, and that the substances described above may be blended in anti-aging cosmetic preparations, and the like.

However, in the cases of the skin aging, cellular proliferative potential of fibroblast decreasing with age, such as the lowering of a cell division rate of the fibroblasts, occurs. With the conventional agents for growing fibroblasts, the problems are encountered in that, though the conventional agents for growing fibroblasts are effective for young fibroblasts, the conventional agents for growing fibroblasts are not always capable of exhibiting a sufficient growth promoting effect with respect to aged fibroblasts. Thus there is a strong demand for development of a novel substance which is capable of enhancing the growth of the aged fibroblasts.

It has been known that a yeast extract has a collagen production promoting action (in patent literature 3), a moisturizing effect (in patent literature 4), a cell activating action, and a hyaluronic acid production promoting action (in patent literature 5). The yeast extract is blended in external preparations for skin, such as the cosmetic preparations.

In the field of Chinese medicine, it has been known that a safflower extract has a vitiated blood improving action. For the purposes of beauty culture, the safflower extract is used for improvement of the cold of the whole body (improvement of blood flow at skin distal areas), the improvement of a pimple, and treatment for atopic dermatitis (in patent literature 6). Also, it has been reported that the safflower extract has elastase inhibitory activity (in patent literature 7). Further, the safflower extract is blended in an anti-aging external preparation for skin, or the like, for obtaining a cell activating action (in patent literature 8).

RELATED ART LITERATURES

[Patent Literature 1]
Japanese Unexamined Patent Publication No. 2008-184441
[Patent Literature 2]
Japanese Patent No. 3748941
[Patent Literature 3]
International Patent Publication No. WO 2004/075621
[Patent Literature 4]
Japanese Patent Publication No. 6 (1994)-23088
[Patent Literature 5]
Japanese Unexamined Patent Publication No. 8 (1996)-163983
[Patent Literature 6]
Japanese Patent No. 3839438
[Patent Literature 7]
Japanese Unexamined Patent Publication No. 2000-319189
[Patent Literature 8]
Japanese Patent No. 3641699

The primary object of the present invention is to provide an agent for growing fibroblasts, which is capable of enhancing growth of not only young fibroblasts but also aged fibroblasts, and which is safe and effective.

DISCLOSURE OF THE INVENTION

The inventors have found that, in cases where a yeast extract and a safflower extract are used in combination, cell growth is capable of being promoted markedly even with respect to aged fibroblasts. The present invention is based upon the findings described above. For example, as described in patent literature 8 cited above, each of the yeast extract and the safflower extract has heretofore been known as a cell activating agent. However, nothing has heretofore been reported as to the effect on the fibroblasts, the cellular proliferative potential of which has become decreased with age. Unexpectedly, in cases where the two constituents described above are used in combination, the growth of the aged fibroblasts is capable of being enhanced synergistically.

The present invention provides an agent for growing fibroblasts, containing a yeast extract and a safflower extract as effective constituents.

The present invention also provides a method of growing fibroblasts wherein a yeast extract and a safflower extract are used.

The present invention further provides an anti-aging agent for skin, containing a yeast extract and a safflower extract as effective constituents.

In cases where the yeast extract or the safflower extract is used alone, a sufficient effect of promoting the growth is not obtained with respect to the aged fibroblasts. However, in cases where the two constituents described above are used in combination, a large effect of promoting the cell growth is obtained with respect to the aged fibroblasts as well as with respect to the young fibroblasts. Therefore, the skin aging is prevented effectively.

The term "aged fibroblasts" as used herein means the fibroblasts which have suffered from the decreasing in functions, such as the cellular proliferative potential and the extracellular matrix producing capability, with age or due to adverse effects of ultraviolet light, active oxygen, and the like.

The yeast extract should preferably be the yeast extract having been prepared from the yeast, which has been cultured in a nutrient culture medium containing glycosaminoglycan and has been subjected to ultraviolet light irradiation processing and/or hydrogen peroxide processing. It has been found that, in cases where the yeast is cultured in the glycosaminoglycan-containing nutrient culture medium in the presence of a stress due to ultraviolet light and/or hydrogen peroxide, a cell protecting constituent is produced. By use of the yeast extract having been prepared from the cultured yeast as described above, the growth of the fibroblasts is enhanced more effectively.

The present invention still further provides an external preparation for skin, containing the agent for growing fibroblasts in accordance with the present invention. For example, in cases where the agent for growing fibroblasts in accordance with the present invention is blended in the external preparation for skin, such as a cosmetic preparation, it is possible to prevent or improve the decrease of the function and number of the fibroblasts in the binding tissue of the derma with age, and the like, and to effectively prevent or improve the symptoms of the skin aging, such as the occurrence of the wrinkles and the sagging, and the lowering of the suppleness and the elasticity.

In accordance with the present invention, wherein the yeast extract and the safflower extract are used in combination, the large effect of promoting the cell growth is obtained with respect to not only the young fibroblasts but also the aged fibroblasts. Also, the fibroblasts in the derma of the aged skin are multiplied, and the suppleness and the elasticity of the skin are enhanced in a safe and effective manner, such that no adverse effect may occur on the skin. Therefore, by the application of the agent for growing fibroblasts in accordance with the present invention or the external preparation for skin, which contains the agent for growing fibroblasts in accordance with the present invention, to the skin, the symptoms of the skin aging, such as the occurrence of wrinkles and sagging, and the lowering of the suppleness and the elasticity, are prevented or improved effectively.

BRIEF DESCRIPTION OF THE DRAWING

FIG. 1 is a graph showing an effect of a combination of a safflower extract and a yeast extract upon growth of young or aged fibroblasts.

BEST MODE FOR CARRYING OUT THE INVENTION

The agent for growing fibroblasts, or the like, in accordance with the present invention contains the yeast extract and the safflower extract as the effective constituents.

As the yeast extract, it is possible to employ an extract of the yeast with a polar solvent; a yeast decomposition product, which results from bacteriolysis of the yeast with self-digestion, acidolysis, enzymatic hydrolysis, or the like, and which has been subjected to filtration; or an extract obtained from processing, in which the yeast decomposition product as described above is dried and then subjected to extraction with a polar solvent, or the like.

As a fungus body for the preparation of the yeast extract, it is possible to employ preferably an *Ascomycetes* yeast, e.g., a yeast of a genus belonging to an Endomycetaceae family, such as an *Eremascus* genus or an *Endomyces* genus; a yeast of a genus belonging to a Saccharomycetaceae family, such as a *Schizosaccharomyces* genus, a *Nadsonia* genus, a *Saccharomycodes* genus, a *Hanseniaspora* genus, a *Wickerhamia* genus, a *Saccharomyces* genus, a *Kluyveromyces* genus, a *Lodderomyces* genus, a *Wingea* genus, an *Endomycopsis* genus, a *Pichia* genus, a *Hansenula* genus, a *Pachysolen* genus, a *Citeromyces* genus, a *Debaryomyces* genus, a *Schwanniomyces* genus, a *Dekkera* genus, a *Saccharomycopsis* genus, or a *Lipomyces* genus; or a yeast of a genus belonging to a Spermophthoraceae family, such as a *Spermaphthora* genus, an *Eremothecium* genus, a *Crebrothecium* genus, an *Ashbya* genus, a *Nematospora* genus, a *Metschnikowia* genus, or a *Coccidiascus* genus. Particularly, from the view point of availability, and the like, the yeast extract should preferably be prepared from a fungus body, such as the yeast of the *Saccharomyces* genus, e.g., a beer yeast, a sake yeast, or a baker's yeast. In the present invention, it is also possible to employ a yeast extract commercially available under the trade name of "Yeast Extract."

As a solvent for the extraction, it is possible to employ water; physiological saline; a phosphate buffer; phosphate buffered saline; a polar organic solvent, e.g., a lower alcohol, such as methanol, ethanol, propanol, or isopropanol; a polyhydric alcohol, such as 1,3-butylene glycol, propylene glycol, dipropylene glycol, or glycerol; an ether, such as diethyl ether or dipropyl ether; an ester, such as ethyl acetate or butyl acetate; or a ketone, such as acetone or ethyl methyl ketone. One kind of the solvent or at least two kinds of the solvents selected from the above-enumerated solvents are used. In cases where solvent extraction is performed, the yeast or the yeast decomposition product may be subjected to freeze-drying and/or pulverizing and may then be subjected to the extraction. Also, homogenizing may be performed in the extraction solvent, and ultrasonic crushing may be performed. The extraction temperature ordinarily falls within the range of approximately 0° C. to a temperature equal to at most the boiling temperature of the solvent. Also, the extraction time varies in accordance with the kind of the extraction solvent and the extraction temperature and ordinarily falls within the range of approximately one hour to approximately five days.

In the present invention, as the yeast extract, it is possible to use preferably the yeast extract having been prepared from the yeast, which has been cultured in the nutrient culture medium containing glycosaminoglycan and has been subjected to the ultraviolet light irradiation processing and/or the hydrogen peroxide processing. It has been found that, in cases where the yeast is cultured in the presence of a stress due to ultraviolet light and/or hydrogen peroxide, the cell protecting constituent, which protects the cells from the stress, is produced. Further, in such cases, by the addition of nutrient peptone, glycosaminoglycan, or the like, to the culture medium, the response to the stress is enhanced. A process for producing the yeast extract, or the like, is described in, for example, U.S. Pat. No. 6,461,857. For example, the yeast extract may be prepared with a process, wherein a *Saccharomyces cerevisiae* yeast, which is one kind of the baker's yeast, is cultured in a nutrient culture medium having been added with non-animal derived glycosaminoglycan, wherein a stress is loaded to the cultured yeast by the addition of hydrogen peroxide in a sublethal proportion, e.g. in a proportion falling within the range of approximately 0.1% by mass to 2% by mass with respect to the total mass of the cultured yeast, and optionally by the irradiation of a sublethal dose of the ultraviolet light (e.g., UVA/UVB irradiation with an intensity of 31.5 $mJ/cm^2$), and wherein the cultured yeast having thus been obtained is solubilized by self-digestion, acidolysis, or the like, and is then subjected to drying, extraction with water, filtration, and the like. Also, a yeast extract having been prepared from a yeast, which has been cultured in a culture medium containing non animal derived glycosaminoglycan and has been subjected to the ultraviolet light irradiation processing and the hydrogen peroxide processing, is commercially supplied under the trade name "Biodyne EMPP (trademark)" by Arch Personal Care Products L. P.

The safflower extract may be prepared by performing solvent extraction of a safflower (*Carthamus tinctorius* L.). It is possible to use each of parts of the safflower, such as a flower, a leaf, a stalk, a root stalk, and a root, or the whole of the safflower. It is preferable to use the flower of the safflower used as a crude drug "Kouka (Carthami Flos.)".

The safflower may be subjected to the extracting operation in a crude state. However, from the view point of the extraction efficiency, the extraction should preferably be performed after the processing, such as slicing, drying, or pulverizing, has been performed. The extraction is performed by dipping in the extraction solvent. In order for the extraction efficiency to be enhanced, stirring may be performed, or the homogenizing may be performed in the extraction solvent. The extraction temperature ordinarily falls within the range of approximately 5° C. to a temperature equal to at most the boiling temperature of the solvent. Also, the extraction time ordinarily falls within the range of approximately four hours to approximately 14 days.

As the extraction solvent; it is possible to employ water; physiological saline; a phosphate buffer; phosphate buffered saline; a polar organic solvent, e.g., a lower alcohol, such as methanol, ethanol, propanol, isopropanol, or butanol; a polyhydric alcohol, such as 1,3-butylene glycol, propylene glycol, dipropylene glycol, 1,2-pentanediol, or glycerol; an ether, such as ethyl ether or propyl ether; an ester, such as ethyl acetate or butyl acetate; or a ketone, such as acetone or ethyl methyl ketone; or a mixed solvent containing at least two kinds of the solvents selected from the above-enumerated solvents.

For example, in the present invention, it is possible to use preferably a safflower extract having been obtained from the processing wherein the flower of the safflower is subjected to the extraction with 50% 1,3-butylene glycol and the filtration. Also, an extract commercially available as the safflower extract may be used in the present invention.

As the agent for growing fibroblasts, or the like, in accordance with the present invention, the yeast extract and the safflower extract may be employed directly. Alternatively, the agent for growing fibroblasts, or the like, in accordance with the present invention may be used in an arbitrary form, such as a solution, a suspension, an emulsion, a cream agent, an ointment agent, a gel agent, or a powdered medicine, by the addition of an arbitrary appropriate auxiliary, such as a carrier, a diluting agent, a stabilizing agent: a buffer agent, a pH adjusting agent, or a solvent. Also, the agent for growing fibroblasts, or the like, in accordance with the present invention may be encapsulated in a liposome, a micro-capsule, or the like. Further, besides the essential constituents described above, the agent for growing fibroblasts, or the like, in accordance with the present invention may be added with a stabilizing agent and an absorption promoting agent, such as an anti-oxidizing agent, an antiseptic agent, or a ultraviolet light absorbing agent, such that the effects of the present invention may not be affected adversely.

The agent for growing fibroblasts, or the like, in accordance with the present invention may be contained in an external preparation base, or the like, and the external preparation for skin may thereby be prepared.

In so far as the effects of the present invention are accomplished, no limitation is imposed upon the blending proportion of each of the yeast extract and the safflower extract in the external preparation for skin in accordance with the present invention. However, the blending proportion of the yeast extract with respect to the total mass of the external preparation should preferably fall within the range of 0.00001% by mass to 10% by mass, should more preferably fall within the range of 0.001% by mass to 5% by mass, and should most preferably fall within the range of 0.005% by mass to 1% by mass. Also, the blending proportion of the safflower extract with respect to the total mass of the external preparation should preferably fall within the range of 0.00001% by mass to 10% by mass, should more preferably fall within the range of 0.001% by mass to 5% by mass, and should most preferably fall within the range of 0.01% by mass to 1% by mass.

The external preparation for skin in accordance with the present invention may embrace cosmetic preparations, pharmaceutical preparations, quasi-drugs, and the like, and may more preferably be applied broadly to the cosmetic preparations. Also, the external preparation for skin in accordance with the present invention may take on an arbitrary preparation form, such as an aqueous solution type, a solubilized type, an emulsion type, an oily liquid type, a gel type, a paste type, an ointment type, an aerosol type, a water-oil two layer type or a water-oil-powder three layer type. Further, the external preparation for skin in accordance with the present invention may take on a form carried by a sheet-shaped base material.

Furthermore, the external preparation for skin in accordance with the present invention may take on an arbitrary product form and may be used for an arbitrary use application, such that the effects of the present invention may be achieved. For example, the external preparation for skin in accordance with the present invention may be applied to basic skin care cosmetics, such as a cleansing preparation, a cosmetic lotion, a cosmetic base lotion or cream, a milky lotion, a cream, a gel, an essence (a beauty liquid), a pack, or a mask; a make-up cosmetic preparation, such as a foundation; a sunscreen cosmetic preparation, such as a sunscreen lotion or cream; a body cosmetic preparation, such as a hand lotion or cream, a leg lotion or cream, or a body lotion or cream; or a toiletry product, such as a body soap or a toilet soap.

If necessary, besides the essential constituents described above, the external preparation for skin in accordance with the present invention may be blended appropriately with a different arbitrary constituent ordinarily used in external preparations for skin, such as cosmetic preparations and pharmaceutical preparations, and may be produced by a conventional procedure in accordance with the desired preparation form. For example, if necessary, the external preparation for skin in accordance with the present invention may be blended appropriately with a whitening agent, a moisturizing agent, an anti-oxidizing agent, an oily constituent, an ultraviolet light absorbing agent, a surface-active agent, a thickening agent, an alcohol, a powder constituent, a coloring agent, an aqueous constituent, water, or a skin nutrient agent. Also, it is possible to blend appropriately a sequestering agent, such as an edetic acid disodiuni salt, an edetic acid trisodium salt, a sodium citrate, sodium polyphosphate, sodium metaphosphate, or gluconic acid; a medicine, such as caffeine, tannin, verapamil, tranexamic acid or a derivative thereof, a licorice extract, glabridin, a hot water extract of a fruit of narrow leaf-firetharm (*Pyracantha angustifolia* Schneid.), a crude drug, tocopheryl acetate, glycyrrhizinic acid or a derivative thereof or a salt thereof; a whitening agent, such as vitamin C, magnesium ascorbyl phosphate, ascorbyl glucoside, arbutin, or kojic acid; or a saccharide, such as glucose, fructose, mannose, sucrose, or trehalose.

EXAMPLES

The present invention will further be illustrated by the following non-limitative examples. In the examples described below, Biodyne EMPP (trademark) (supplied by Arch Personal Care Products L. P.) was employed as the yeast extract, and Pharcolex Safflower B (supplied by ICHIMARU PHARCOS Co., Ltd.) was employed as the safflower extract.
Study of Effect of Promoting Growth of Fibroblasts Fibroblasts having been derived from the human newborn foreskin were used as "young fibroblasts", and fibroblasts having been derived from the derma of the skin of a septuagenarian female were used as "aged fibroblasts".

As for each of the young fibroblasts and the aged fibroblasts, the fibroblasts were cultured in a 10% FBS-containing DMEM culture medium for 24 hours. Thereafter, the culture medium was replaced by a 0.5% FBS-containing DMEM culture medium, which had been added with 0.1% of a safflower extract, a 0.5% FBS containing DMEM culture medium, which had been added with 0.01% of a yeast extract, or a 0.5% FBS-containing DMEM culture medium, which had been added with 0.1% of the safflower extract and 0.01% of the yeast extract, and the fibroblasts were cultured still further for 48 hours. Also, as a control, the culture processing was performed in the same manner in a 0.5% FBS-containing DMEM culture medium, which had not been added with the test substance. At the time of the end of the culture processing, respiration activity of the fibroblasts was measured by use of an Alamar Blue reagent and was used as an index for the growth of the fibroblasts. A relative fibroblast growth (%) was calculated with respect to the respiration activity of the control, which was taken as 100%.

The results illustrated in FIG. 1 were obtained. With the safflower extract alone, as for both of the young fibroblasts and the aged fibroblasts, the growth of the fibroblasts was enhanced slightly, and the effect of promoting the growth of the fibroblasts was small. Also, with the yeast extract alone, the growth of the young fibroblasts was enhanced markedly, but the effect of promoting the growth of the fibroblasts with respect to the aged fibroblasts was small. However, by the addition of the safflower extract and the yeast extract in combination, the effect of promoting the growth of the fibroblasts, particularly with respect to the aged fibroblasts, was enhanced synergistically, and the growth of the aged fibroblasts was enhanced to a level equivalent to the level of the growth of the young fibroblasts.

It was suggested that, by the use of the safflower extract and the yeast extract in combination, the growth of the aged fibroblasts, the cellular proliferative potential of which had lowered with age, was enhanced markedly, the growth of the fibroblasts was enhanced even in the cases of the aged skin, and the symptoms of the skin aging, such as the occurrence of wrinkles and sagged skin, and the lowering of the suppleness and the elasticity, were prevented or improved effectively.

Examples for the external preparation for skin containing the agent for growing fibroblasts in accordance with the present invention will be illustrated hereinbelow. The blending proportions were expressed in terms of % by mass with respect to the total mass of the composition.

| Example 1 (w/o cream) | (% by mass) |
| --- | --- |
| (1) Dimethylpolysiloxane | 3.0 |
| (2) Decamethylcyclopentasiloxane | 13.0 |
| (3) Dodecamethylcyclohexasiloxane | 5.0 |
| (4) Polyoxyethylene-methylpolysiloxane copolymer | 1.0 |
| (5) 3-Tris(trimethylsiloxy)silylpropylcarbamic acid pullulan | 1.0 |
| (6) Decamethylcyclopentasiloxane blend of crosslinked type polymethylsiloxane (Dow Corning 9040 Silicone Elastomer Blend TM, supplied by Dow Corning Co., Ltd.) | 5.0 |
| (7) Retinol acetate | 0.1 |
| (8) Para-hydroxybenzoic acid ester | Appropriate quantity |
| (9) L-Menthol | Appropriate quantity |
| (10) Trimethylsiloxysilicic acid | 2.0 |
| (11) Ethanol | 2.0 |
| (12) Glycerol | 3.0 |
| (13) Dipropylene glycol | 5.0 |
| (14) Polyethylene Glycol 6000 | 5.0 |
| (15) Sodium hexametaphosphate | 0.05 |
| (16) Tocopherol acetate | 0.1 |
| (17) Caffeine | 0.1 |
| (18) Fennel extract | 0.1 |
| (19) *Hamamelis* extract | 0.1 |
| (20) Safflower extract | 1.0 |
| (21) Yeast extract | 1.0 |
| (22) Edetic acid trisodium salt | 0.05 |
| (23) Dimorpholinopyridazinone | 0.01 |
| (24) Trimethoxycinnamic acid methylbis(trimethylsiloxy)silylisopentyl | 0.1 |
| (25) Inorganic composite particles (Cover Leaf AR-80TM, supplied by JGC Catalysts and Chemicals Ltd.) | 5.0 |
| (26) Yellow iron oxide | Appropriate quantity |
| (27) Cobalt titanate | Appropriate quantity |
| (28) Dimethyldistearylammonium hectorite | 1.5 |
| (29) Polyvinyl alcohol | 0.1 |
| (30) Hydroxyethyl cellulose | 0.1 |
| (31) Sodium acrylate/2-acrylamido-2-methylpropanesulfonic acid copolymer (SIMULGEL EGTM, supplied by SEPPIC Co., Ltd.) | 0.1 |
| (32) (Acryloyldimethyltaurineammonium/VP) copolymer (Aristoflex AVCTM, supplied by Clariant Co., Ltd.) | 0.1 |
| (33) Perfume | Appropriate quantity |
| (34) Deionized water | Remainder |

| Example 2 (milky lotion) | (% by mass) |
| --- | --- |
| Petrolatum | 5 |
| Behenyl alcohol | 0.5 |
| Batyl alcohol | 0.5 |
| Glycerol | 7 |
| 1,3-Butylene glycol | 7 |
| 1,2-Pentanediol | 1 |
| Xylitol | 3 |
| Polyethylene Glycol 20000 | 2 |
| Hydrogenated oil | 2 |
| Jojoba oil | 2 |
| Squalane | 5 |
| Isostearic acid | 0.5 |
| Tetra-2-ethylhexanoic acid pentaerythritol | 2 |
| Polyoxyethylene hydrogenated caster oil | 0.5 |

| Example 2 (milky lotion) | (% by mass) |
|---|---|
| Lauryldimethylaminoacetic acid betaine | 0.4 |
| Potassium hydroxide | Appropriate quantity |
| Sodium pyrosulfite | 0.01 |
| Sodium hexametaphosphate | 0.05 |
| Dipotassium glycyrrhizinate | 0.05 |
| Trimethylglycine | 3 |
| Arbutin | 3 |
| Yeast extract | 0.1 |
| Tocopherol acetate | 0.1 |
| Thiotaurine | 0.1 |
| Safflower extract | 1 |
| *Sophora flavescens* extract | 0.1 |
| Red iron oxide | Appropriate quantity |
| Quince seed extract | 0.1 |
| Carboxyvinyl polymer | 0.2 |
| Phenoxy ethanol | Appropriate quantity |
| Deionized water | Remainder |

| Example 3 (milky lotion) | (% by mass) |
|---|---|
| Dimethylpolysiloxane | 3 |
| Decamethylcyclopentasiloxane | 4 |
| Ethanol | 5 |
| Glycerol | 6 |
| 1,3-Butylene glycol | 5 |
| Polyoxyethylenemethylglucoside | 3 |
| Sunflower oil | 1 |
| Squalane | 2 |
| Potassium hydroxide | 0.1 |
| Sodium hexametaphosphate | 0.05 |
| Hydroxypropyl-β-cyclodextrin | 0.1 |
| Dipotassium glycyrrhizinate | 0.05 |
| Loquat leaf extract | 0.1 |
| Monosodium glutamate | 0.05 |
| Fennel extract | 0.1 |
| Yeast extract | 0.1 |
| Lavender oil | 0.1 |
| Safflower extract | 0.1 |
| *Rehmannia Chinensis* Root Extract | 0.1 |
| Dimorpholinopyridazinone | 0.1 |
| Xanthan gum | 0.1 |
| Carboxyvinyl polymer | 0.1 |
| Acrylic acid-alkyl methacrylate copolymer (PEMULEN TR-1) | 0.1 |
| Red iron oxide | Appropriate quantity |
| Yellow iron oxide | Appropriate quantity |
| Paraben | Appropriate quantity |
| Deionized water | Remainder |

The external preparation for skin of each of the examples described above exhibited the excellent effect of improving wrinkles by being applied to the aged skin.

The invention claimed is:

1. A method for promoting the growth of fibroblasts contained in human skin, comprising:
   providing an agent that comprises 0.005% by mass to 1% by mass of a yeast extract and 0.001% by mass to 1% by mass of a safflower extract as effective constituents, wherein the yeast extract is an extract having been prepared from a yeast of the *Saccharomyces* genus, which has been cultured in a nutrient culture medium containing glycosaminoglycan and has been subjected to ultraviolet light irradiation processing and/or hydrogen peroxide processing, and wherein the safflower extract is a solvent extract of the flower of the safflower; and
   applying the agent in the form of an external preparation to the human skin.

2. The method as defined in claim 1, wherein the solvent used to extract the safflower extract from the flower of the safflower is 1,3-butylene glycol.

3. A method for reducing the occurrence of wrinkles in human skin caused by aging, the method comprising:
   providing an agent that comprises 0.005% by mass to 1% by mass of a yeast extract and 0.01% by mass to 1% by mass of a safflower extract as effective constituents, wherein the yeast extract is an extract having been prepared from a yeast of the *Saccharomyces* genus, which has been cultured in a nutrient culture medium containing glycosaminoglycan and has been subjected to ultraviolet light irradiation processing and/or hydrogen peroxide processing, and wherein the safflower extract is a solvent extract of the flower of the safflower; and
   applying the agent in the form of an external preparation to the human skin to promote the growth of fibroblasts contained in the human skin.

4. The method as defined in claim 3, wherein the solvent used to extract the safflower extract from the flower of the safflower is 1,3-butylene glycol.

* * * * *